(12) United States Patent
Morgas et al.

(10) Patent No.: US 12,318,633 B2
(45) Date of Patent: Jun. 3, 2025

(54) DETERMINING UNCERTAINTY IN RADIATION THERAPY DELIVERED DOSE ACCUMULATION

(71) Applicant: SIEMENS HEALTHINEERS INTERNATIONAL AG, Steinhausen (CH)

(72) Inventors: Tomasz Morgas, Basel (CH); Tobias Gass, Vogelsang AG (CH); Thomas Coradi, Lenzburg (CH); Fernando Franco, Zurich (CH); Michael Waschbüesch, Rheinfelden (CH)

(73) Assignee: SIEMENS HEALTHINEERS INTERNATIONAL AG (CH)

( * ) Notice: Subject to any disclaimer, the term of this patent is extended or adjusted under 35 U.S.C. 154(b) by 241 days.

(21) Appl. No.: 17/710,975

(22) Filed: Mar. 31, 2022

(65) Prior Publication Data
US 2023/0310896 A1 Oct. 5, 2023

(51) Int. Cl.
*A61N 5/10* (2006.01)
(52) U.S. Cl.
CPC ................... *A61N 5/1071* (2013.01)
(58) Field of Classification Search
CPC ....... A61N 5/1071; A61N 5/1031; A61N 5/10
See application file for complete search history.

(56) References Cited

U.S. PATENT DOCUMENTS

| | | | | |
|---|---|---|---|---|
| 9,987,504 | B2 * | 6/2018 | Nord | A61N 5/103 |
| 10,029,121 | B2 * | 7/2018 | Li | A61B 5/055 |
| 10,279,196 | B2 * | 5/2019 | West | A61N 5/1031 |
| 10,475,537 | B2 * | 11/2019 | Purdie | A61N 5/103 |

(Continued)

OTHER PUBLICATIONS

International Search Report and Written Opinion of the International Searching Authority, International application No. PCT/EP2023/057989, Jun. 26, 2023.

(Continued)

*Primary Examiner* — Tung S Lau
(74) *Attorney, Agent, or Firm* — SU IP CONSULTING

(57) ABSTRACT

A computer-implemented method of generating dose information for a region of patient anatomy includes determining a first set of dose values for a first three-dimensional (3D) image of the region, wherein each value in the first set of dose values is associated with a different voxel of the first 3D image, and wherein the first 3D image is associated with a specific application of dose to the region; determining a second set of dose values for a representative 3D image of the region, wherein each value in the second set of dose values is associated with a different voxel of the representative 3D image; determining a set of geometric error models for the representative 3D image of the region, wherein each geometric error model in the set of geometric error models indicates a geometric error between a voxel of the representative 3D image and one or more voxels of a treatment fraction 3D image of the region; and based on the second set of dose values and the set of geometric error models, determining a set of dose probability values for each voxel of the representative 3D image, wherein each set of dose probability values includes at least one dose value and a probability value that corresponds to the dose value.

20 Claims, 13 Drawing Sheets

(56) References Cited

U.S. PATENT DOCUMENTS

| | | | | |
|---|---|---|---|---|
| 2009/0234626 A1* | 9/2009 | Yu | ............ | G16H 50/50 |
| | | | | 703/11 |
| 2014/0105355 A1* | 4/2014 | Toimela | ............ | A61N 5/1064 |
| | | | | 382/132 |
| 2016/0287906 A1* | 10/2016 | Nord | ............ | A61N 5/103 |
| 2017/0203126 A1* | 7/2017 | Dempsey | ............ | A61N 5/1049 |
| 2018/0211725 A1* | 7/2018 | Purdie | ............ | G16H 10/60 |

OTHER PUBLICATIONS

Neil Kirby et al., "An Automated Deformable Image Registration Evaluation of Confidence Tool", Physics in medicine and biology, Mar. 30, 2016, vol. 61, No. 8.

David Tilly et al., "Fast Dose Algorithm for Generation of Dose Coverage Probability for Robustness Analysis of Fractionated Radiotherapy", Physics in medicine and biology, Jun. 29, 2015, vol. 60, No. 14.

David Tilly et al., "Probabilistic Optimization of Dose Coverage in Radiotherapy", Physic and Imaging in Radiation Oncology, Apr. 1, 2019, vol. 19.

* cited by examiner

DETERMINING UNCERTAINTY IN RADIATION THERAPY DELIVERED DOSE ACCUMULATION

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on the planning target volume that spares the surrounding normal tissue from receiving doses above specified tolerances, thereby minimizing risk of damage to healthy tissue. Prior to the delivery of radiation therapy, an imaging system is typically employed to provide a three-dimensional image of the target tissue and surrounding area, referred to as the "treatment planning image." From such imaging, the size and mass of the target tissue can be estimated, a planning target volume determined, and an appropriate treatment plan generated.

So that the prescribed dose is correctly supplied to the planning target volume (i.e., the target tissue) during radiation therapy, the patient should be correctly positioned relative to the linear accelerator that provides the radiation therapy. Typically, dosimetric and geometric data are checked before and during the treatment, to ensure correct patient placement and that the administered radiotherapy treatment matches the previously planned treatment. This process is referred to as image guided radiation therapy (IGRT), and involves the use of an imaging system to view target tissues immediately before or while radiation treatment is delivered to the planning target volume. IGRT incorporates imaging coordinates from the treatment plan to ensure the patient is properly aligned for treatment in the radiation therapy device.

However, IGRT often cannot compensate for structural and spatial changes that typically occur in patient anatomy during treatment. For instance, during a course of radiotherapy, which can take place over many days, the planning target volume and/or neighboring patient anatomy can change in size or relative position due to tumor shrinkage, patient weight loss, variation in bowel or bladder content, and the like. Consequently, adaptive radiotherapy (ART) has been developed to take into account additional information gained about patient anatomy via day-of-treatment imaging for each treatment fraction. Adaptive radiotherapy enables the treatment to be changed, or adapted, to respond to such additional information indicating that patient anatomy has changed relative to the original state of the anatomy at the time of planning.

SUMMARY

According to various embodiments, the uncertainty in the dose that is accumulated in one or more regions of interest during radiotherapy is determined and provided to the clinician or other user of a radiation therapy system. In the embodiments, the uncertainty of accumulated dose for a given region of interest is quantitatively determined based on geometric error associated with deformable image registration of a day-of-treatment 3D image of patient anatomy to a representative 3D image of patient anatomy. Advantageously, in the embodiments, the uncertainty of accumulated dose can be presented in conjunction with accumulated dose information, thereby providing the clinician with a clear understanding of the uncertainty associated with the propagated and/or accumulated dose for a particular region of interest. For example, for a particular region of interest, best-case, worst-case, and most-likely dosing scenarios, among others, can be presented to the clinician, facilitating clinician understanding of accumulated dose in various applications. For instance, a most-likely accumulated or propagated dose is of particular interest for reporting and understanding clinical outcomes, while a worst-case accumulated or propagated dose is of more interest for the planning of re-treatment.

In some embodiments, a computer-implemented method of generating dose information for a region of patient anatomy includes determining a first set of dose values for a first three-dimensional (3D) image of the region, wherein each value in the first set of dose values is associated with a different voxel of the first 3D image, and wherein the first 3D image is associated with a specific application of dose to the region; determining a second set of dose values for a representative 3D image of the region, wherein each value in the second set of dose values is associated with a different voxel of the representative 3D image; determining a set of geometric error models for the representative 3D image of the region, wherein each geometric error model in the set of geometric error models indicates a geometric error between a voxel of the representative 3D image and one or more voxels of a treatment fraction 3D image of the region; and based on the second set of dose values and the set of geometric error models, determining a set of dose probability values for each voxel of the representative 3D image, wherein each set of dose probability values includes at least one dose value and a probability value that corresponds to the dose value.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
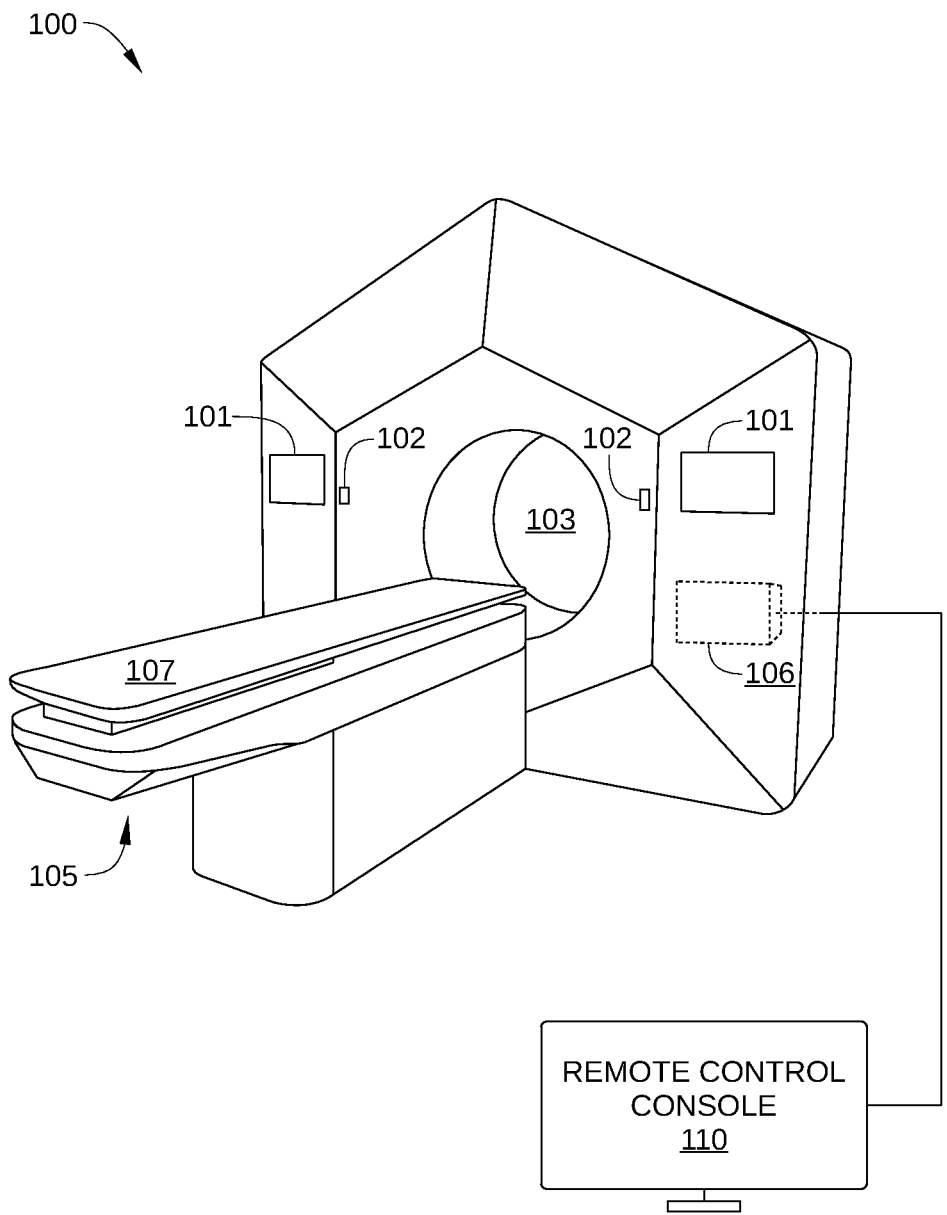
FIG. 1 is a perspective view of a radiation therapy system that can beneficially implement various aspects of the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

Introduction

As noted previously, adaptive radiation therapy (ART) has been developed to take into account additional information gained about patient anatomy via day-of-treatment imaging for each treatment fraction. Thus, each treatment fraction may be changed or adapted based on day-of-treatment anatomical information. As a result, dose can be applied more accurately to the changing geometry of the patient anatomy during each treatment fraction. However, because each adapted treatment fraction departs from the originally planned treatment, reporting of delivered dose for each treatment fraction is problematic.

Specifically, in ART, both the patient anatomy and the dose distribution within the patient anatomy can vary from fraction to fraction. Therefore, accurate reporting of delivered dose to a particular region of interest (ROI) in one treatment fraction involves propagating the dose delivered to the ROI in that treatment fraction to the ROI in a representative three-dimensional (3D) image of the patient anatomy, such as the treatment planning image. For example, deformable image registration may be employed to register the ROI in the current patient geometry to the ROI in the representative 3D image. Thus, the delivered dose for each treatment fraction, which may be applied to a different ROI geometry on a daily basis, can be presented to the clinician with respect to the same representative 3D image. However, propagation of the treatment fraction dose from the actual patient anatomy at the time of treatment to the representative 3D image can introduce significant geometric error, such as deformable registration error. Consequently, there is uncertainty in the dose distribution that is reported via the representative 3D image. Further, such uncertainty is generally increased for the accumulated dose that is reported for multiple treatment fractions. The uncertainty of dose distribution information and accumulated dose information cannot be understood without a separate analysis of the impact of deformable registration errors on dose distribution for each treatment fraction. Thus, clinicians are aware of the possible dose uncertainty, but are typically unable to assess what it is for a particular patient. As a result, clinicians generally do not rely on such accumulated dose information, and can be prevented from performing more accurate planning for re-treatments and from understanding the relationship between clinical outcomes and delivered dose.

In light of the above, there is a need in the art for improved techniques for reporting delivered dose for a specific radiation therapy treatment fraction and accumulated dose for multiple radiation therapy treatment fractions.

System Overview

FIG. 1 is a perspective view of a radiation therapy system 100 that can beneficially implement various aspects of the present disclosure. Radiation therapy (RT) system 100 is a radiation system configured to detect intra-fraction motion in near-real time using X-ray imaging techniques. Thus, RT system 100 is configured to provide stereotactic radiosurgery and precision radiotherapy for lesions, tumors, and conditions anywhere in the body where radiation treatment is indicated. As such, RT system 100 can include one or more of a linear accelerator (LINAC) that generates a megavolt (MV) treatment beam of high energy X-rays, one or more kilovolt (kV) X-ray sources, one or more X-ray imagers, and, in some embodiments, an MV electronic portal imaging device (EPID). By way of example, RT system 100 is described herein configured with a circular gantry. In other embodiments, RT system 100 can be configured with a C-gantry capable of infinite rotation via a slip ring connection.

Generally, RT system 100 is capable of kV imaging of a target volume immediately prior to or during application of an MV treatment beam, so that an IGRT and/or an intensity-modulated radiation therapy (IMRT) process can be performed using X-ray imaging. RT system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. RT system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location.

Figure 2:
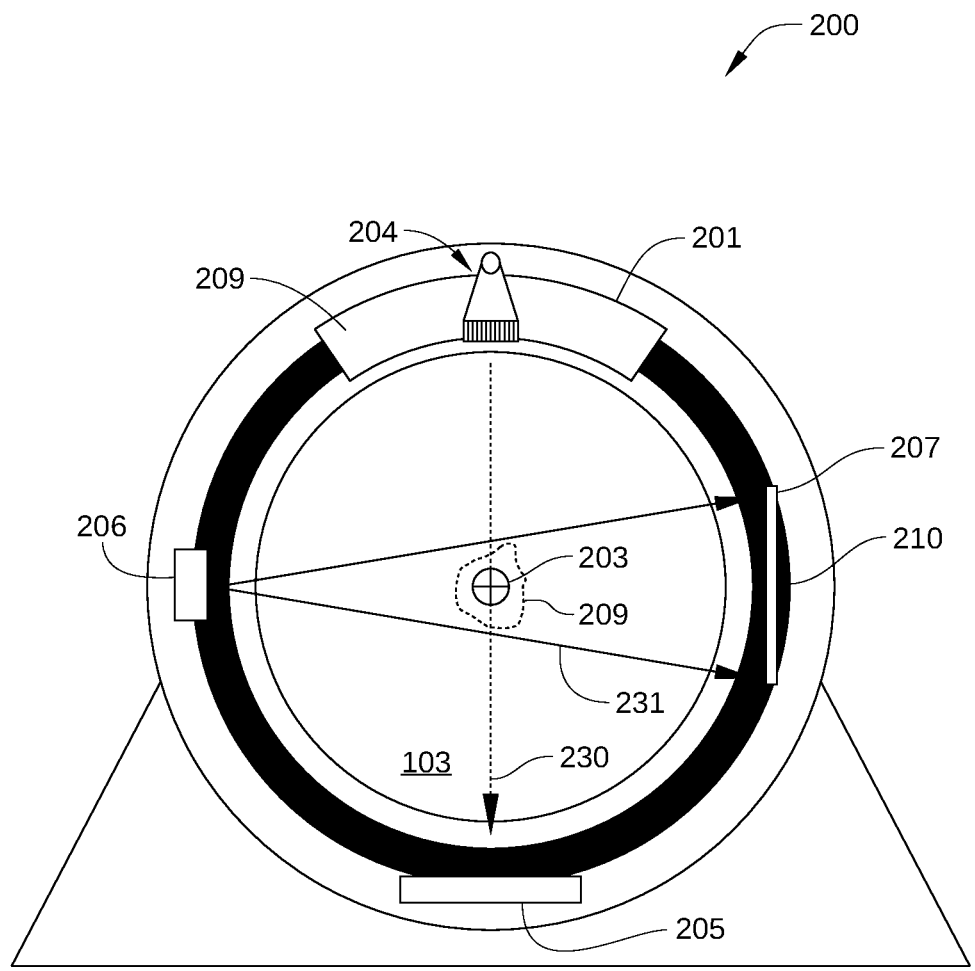
FIG. 2 schematically illustrates a drive stand and gantry of the radiation therapy system of FIG. 1, according to various embodiments of the present disclosure.

FIG. 2 schematically illustrates a drive stand 200 and gantry 210 of RT system 100, according to various embodiments of the present disclosure. Covers, base positioning assembly 105, couch 107, and other components of RT system 100 are omitted in FIG. 2 for clarity. Drive stand 200 is a fixed support structure for components of RT treatment system 110, including gantry 210 and a drive system 201 for rotatably moving gantry 210. Drive stand 200 rests on and/or is fixed to a support surface that is external to RT treatment system 110, such as a floor of an RT treatment facility. Gantry 210 is rotationally coupled to drive stand 200 and is a support structure on which various components of RT system 100 are mounted, including a linear accelerator (LINAC) 204, an MV electronic portal imaging device (EPID) 205, an imaging X-ray source 206, and an X-ray imager 207. During operation of RT treatment system 110, gantry 220 rotates about bore 103 when actuated by drive system 201.

Drive system 201 rotationally actuates gantry 210. In some embodiments, drive system 201 includes a linear motor that can be fixed to drive stand 200 and interacts with a magnetic track (not shown) mounted on gantry 210. In other embodiments, drive system 201 includes another suitable drive mechanism for precisely rotating gantry 210 about bore 201. LINAC 204 generates an MV treatment beam 230 of high energy X-rays (or in some embodiments electrons, protons, and/or other heavy charged particles, ultra-high dose rate X-rays (e.g., for FLASH radiotherapy) or microbeams for microbeam radiation therapy) and EPID 205 is configured to acquire X-ray images with treatment beam 230. Imaging X-ray source 206 is configured to direct a conical beam of X-rays, referred to herein as imaging X-rays 231, through an isocenter 203 of RT system 100 to X-ray imager 207, and isocenter 203 typically corresponds to the location of a target volume 209 to be treated. In the embodiment illustrated in FIG. 2, X-ray imager 207 is depicted as a planar device, whereas in other embodiments, X-ray imager 207 can have a curved configuration.

X-ray imager 207 receives imaging X-rays 231 and generates suitable projection images therefrom. According to certain embodiments, such projection images can then be employed to construct or update portions of imaging data for a digital volume that corresponds to a 3D region that includes target volume 209. That is, a 3D image of such a 3D region is reconstructed from the projection images. In some embodiments, cone-beam computed tomography (CBCT) and/or digital tomosynthesis (DTS) can be used to process the projection images generated by X-ray imager 207. CBCT is typically employed to acquire projection images over a relatively long acquisition arc, for example over a rotation of 180° or more of gantry 210. As a result, a high-quality 3D reconstruction of the imaged volume can be generated. CBCT is often employed at the beginning of a radiation therapy session, such as a treatment fraction, to generate a set-up 3D reconstruction. For example, CBCT may be employed immediately prior to application of treatment beam 230 to generate a 3D reconstruction confirming that target volume 209 has not moved or changed shape. Alternatively, or additionally, in some embodiments, partial-data reconstruction is performed by RT system 100 during portions of an IGRT or IMRT process in which partial image data is employed to generate a 3D reconstruction of target volume 209. For example, as treatment beam 230 is directed to isocenter 203 while gantry 210 rotates through a treatment arc, DTS image acquisitions can be performed to generate image data for target volume 209. Because DTS image acquisition is performed over a relatively short acquisition arc, for example between about 10° and 60°, near real-time feedback for the shape and position of target volume 209 can be provided by DTS imaging during the IGRT process.

In the embodiment illustrated in FIG. 2, RT system 100 includes a single X-ray imager and a single corresponding imaging X-ray source. In other embodiments, RT system 100 can include two or more X-ray imagers, each with a corresponding imaging X-ray source.

The projection images generated by X-ray imager 207 (or by multiple x-ray imagers included in RT system 100) are used to construct imaging data for a digital volume of patient anatomy within a 3D region that includes the target volume. Alternatively or additionally, such projection images can be used to update portions of existing imaging data for the digital volume corresponding to the 3D region. One embodiment of such a digital volume is described below in conjunction with FIG. 3.

Figure 3:
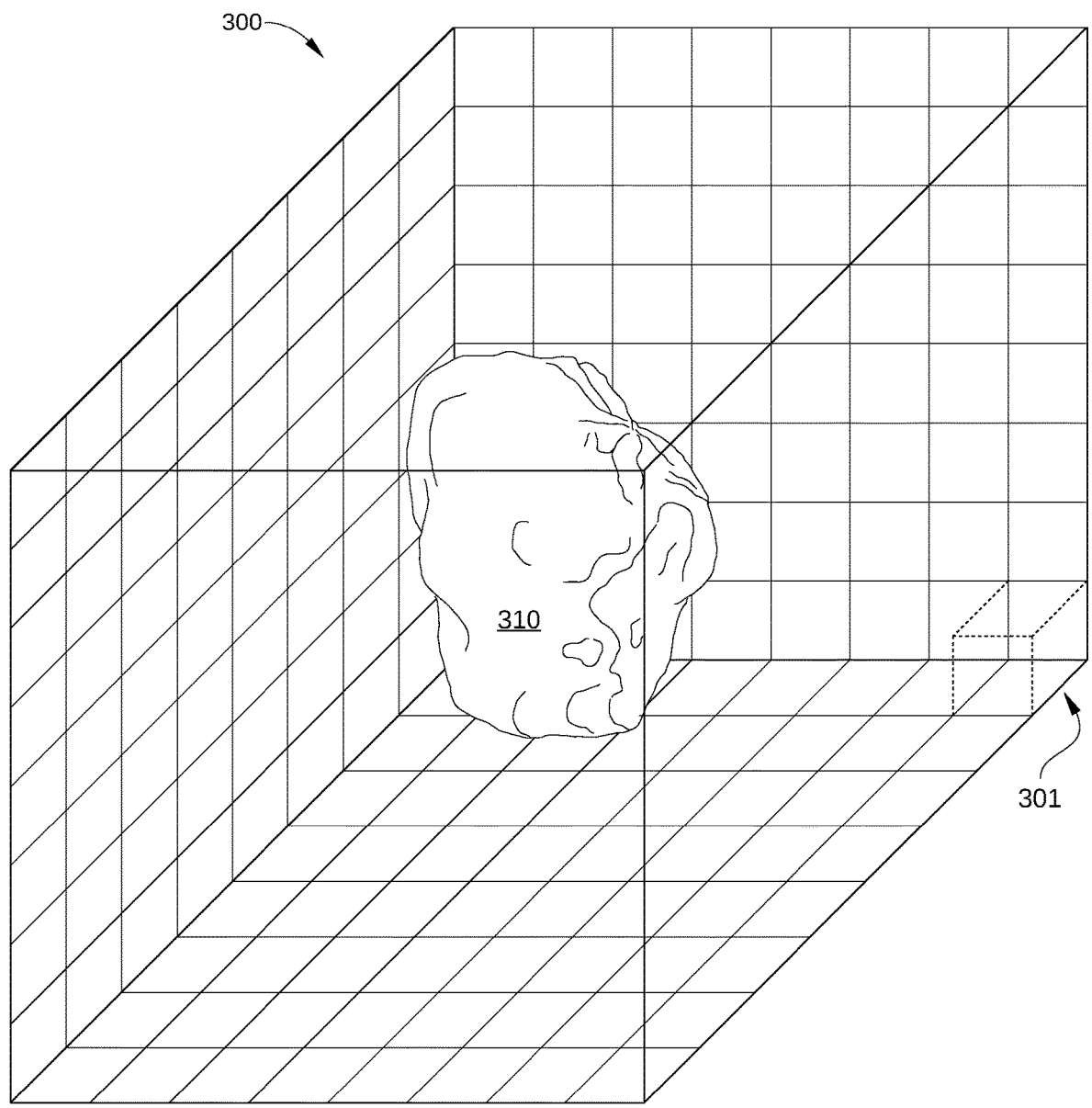
FIG. 3 schematically illustrates a digital volume that is constructed based on projection images generated by one or more X-ray images included in the radiation therapy system of FIG. 1, according to various embodiments of the present disclosure.

FIG. 3 schematically illustrates a digital volume 300 that is constructed based on projection images generated by one or more X-ray imagers included in RT system 100, according to various embodiments of the present disclosure. For example, in some embodiments, the projection images can be generated by a single X-ray imager, such as X-ray imager 207, and in other embodiments the projection images can be generated by multiple X-ray imagers.

Digital volume 300 includes a plurality of voxels 301 (dashed lines) of anatomical image data, where each voxel 301 corresponds to a different location within digital volume 300. For clarity, only a single voxel 301 is shown in FIG. 3. Digital volume 300 corresponds to a 3D region that includes target volume 310. In FIG. 3, digital volume 300 is depicted as an 8×8×8 voxel cube, but in practice, digital volume 300 generally includes many more voxels, for example orders of magnitude more than are shown in FIG. 3.

For purposes of discussion, target volume 310 can refer to the gross tumor volume (GTV), clinical target volume (CTV), or the planning target volume (PTV) for a particular treatment. The GTV depicts the position and extent of the gross tumor, for example what can be seen or imaged; the CTV includes the GTV and an additional margin for sub-clinical disease spread, which is generally not imageable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by X-ray imaging of digital volume 300.

Figure 4:
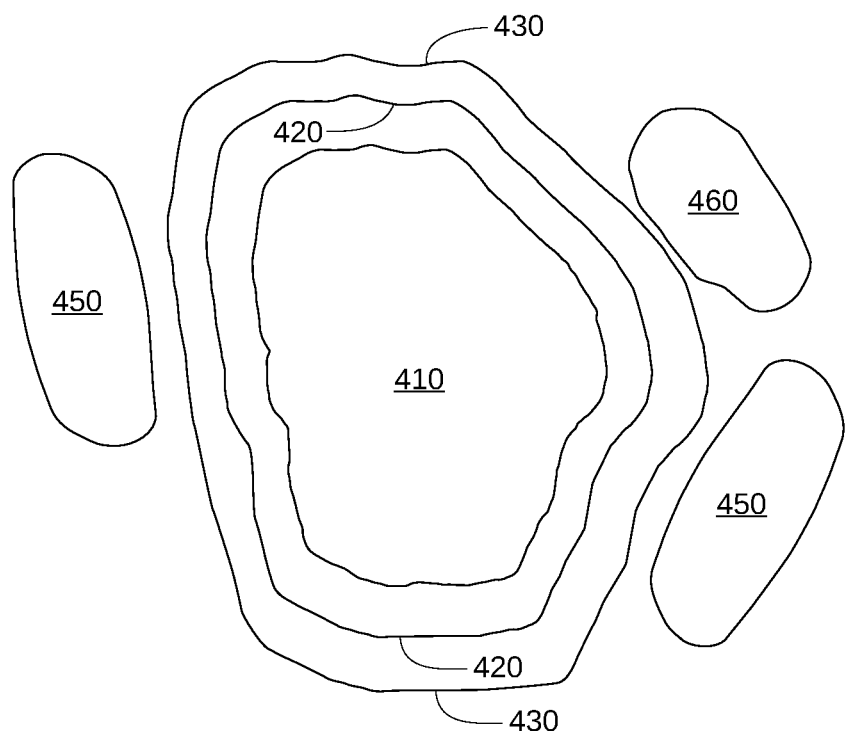
FIG. 4 schematically illustrates examples of various regions of interest.

Generally, a clinician or other user is concerned with delivered dose for various ROIs besides target volume 310, such as organs at risk (OARs) and other critical structures. FIG. 4 schematically illustrates examples of various ROIs. Specifically, FIG. 4 illustrates a GTV 410, a CTV 420, a PTV 430, two OARs 450, and a critical structure 460. It is noted that the structures included in FIG. 4 are depicted in two dimensions, but are generally three-dimensional in nature. As such, GTV 410, CTV 420, PTV 430, OARs 450, and critical structure 460 are each typically defined via a three-dimensional segmentation process, in which a region of specific voxels (not shown in FIG. 4) that are included in a set of treatment planning CT scans is indicated as a particular structure. GTV 410, CTV 420, and PTV 430 are regions or structures that an ideal treatment plan causes to receive at least a minimum threshold dose, while OARs 450 and critical structure 460 are regions or structures of normal tissue that an ideal treatment plan causes to receive as little dose as possible.

Generally, a treatment plan for a particular patient is generated based on a treatment planning CT, such as digital volume 300 of FIG. 3, that includes GTV 410, CTV 420, and/or PTV 430 for that patient. The treatment plan is associated with a treatment site that includes target tissue structures, such as PTV 430, and normal tissue structures that are proximate to the target tissue, such as OARs 450 and/or critical structure 460. These target and normal tissue structures are typically both referenced in treatment planning. For purposes of scoring multiple treatment plans within an optimization process, the treatment planning process may also include specified expansions of the target tissue structures and normal tissue structures. Thus, in addition to GTV 410, a treatment plan may reference CTV 420, the internal target volume (ITV), PTV 430, OARs 450, critical structures 460, and/or a planning OAR volume (PRV), among others. Further, a treatment plan typically specifies a target minimum dose threshold for radiation treatment of PTV 430 and a maximum allowable dose distribution in OARs 450 and/or critical structures 460.

Radiation Therapy Treatment Fractions with Probabilistic Dose Distributions

Ideally, throughout the course of a multi-fraction radiation therapy treatment, a clinician can easily compare the delivered dose for a particular treatment fraction to the above-described target minimum dose threshold for radiation treatment of PTV 430 and the maximum allowable dose distribution for OARs 450 and/or critical structures 460. In addition, clinicians similarly can benefit from comparing the current accumulated dose of multiple treatment fractions to such minimum dose thresholds and maximum allowable dose distributions. However, as noted previously, conventional radiotherapy systems are incapable of determining and presenting the uncertainty of accumulated or propagated dose distribution when ART is employed and a treatment fraction has been changed from the originally planned treatment. Thus, the propagated dose information and accumulated dose information that is currently available to clinicians is of limited utility in the context of ART, since clinicians generally cannot determine the uncertainty associated with such information, and therefore do not make clinical decisions based on such information.

According to various embodiments, the uncertainty in the dose distribution that is propagated in a representative 3D image to one or more ROIs during a particular adaptive radiotherapy treatment fraction is determined and provided to the clinician or other user of a radiation therapy system. Additionally or alternatively, in some embodiments, the uncertainty in the accumulated dose associated with multiple adaptive radiotherapy treatment fractions is determined and provided to the clinician or other user of a radiation therapy system. The embodiments facilitate more accurate planning for re-treatments and enable better clinician understanding of the relationship between an outcome and the actual delivered dose. Examples of such embodiments are described below in conjunction with FIGS. 5-12.

Figure 5:
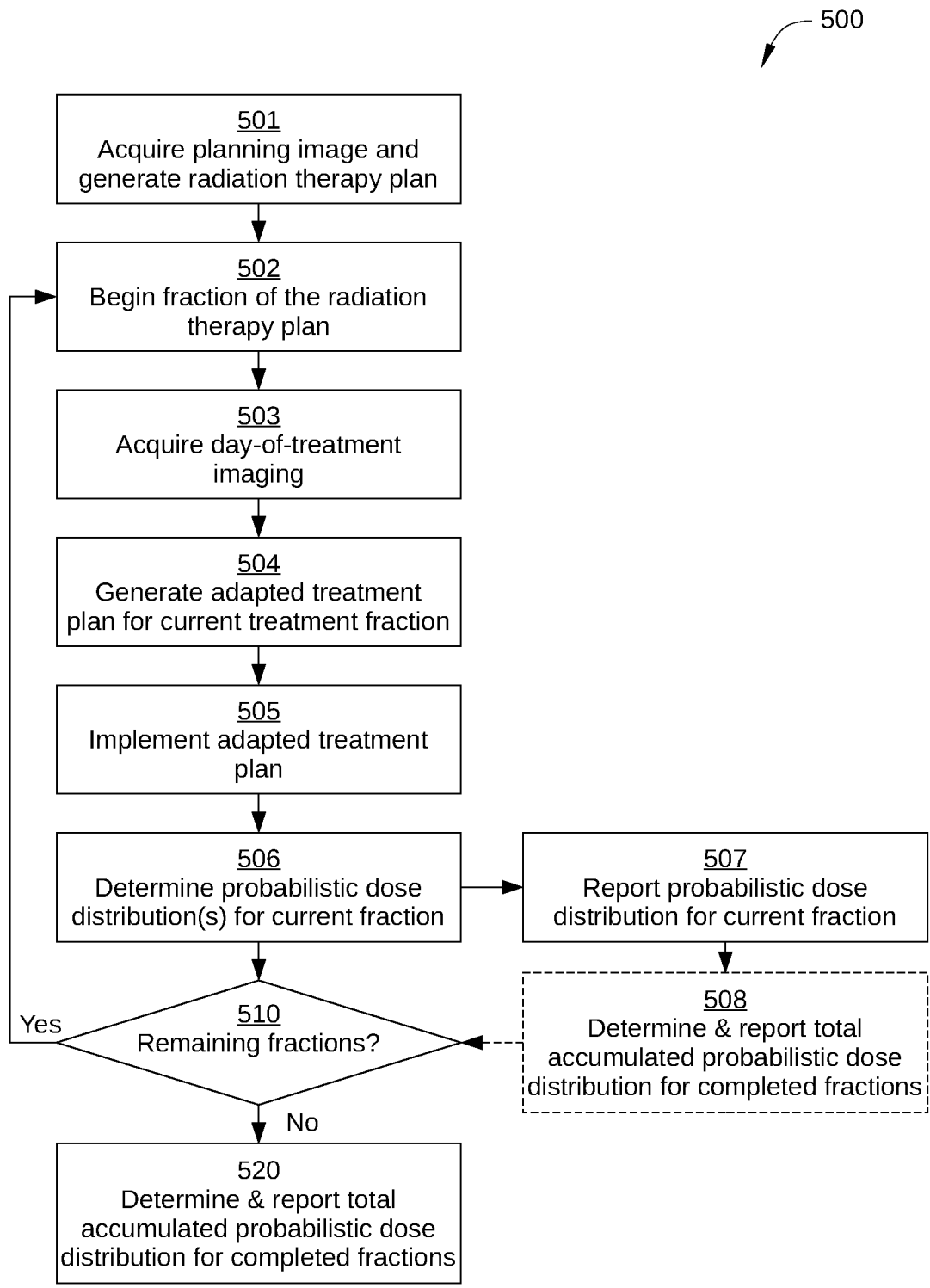
FIG. 5 sets forth a flowchart of an adaptive radiotherapy process, according to various embodiments of the present disclosure.

FIG. 5 sets forth a flowchart of an ART process 500, according to various embodiments of the present disclosure. Unlike conventional ART processes, ART process 500 includes the determination and presentation of probabilistic dose distribution information for each treatment fraction. Alternatively or additionally, in some embodiments ART process 500 includes the determination and presentation of probabilistic accumulated dose information for multiple treatment fractions.

ART process 500 may include one or more operations, functions, or actions as illustrated by one or more of blocks 501-520. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although ART process 500 is described in conjunction with RT system 100 and FIGS. 1-4, persons skilled in the art will understand that any suitably configured radiation therapy system and/or computing device is within the scope of the present embodiments.

In step 501, treatment planning images are acquired of a particular patient and a radiation therapy plan is generated for that patient. For example, in some embodiments, a treatment planning CT (and/or other treatment planning imaging) is specified and performed that shows the ROIs of the patient anatomy, such as a tumor, a region of anatomy around the tumor, OARs, critical structures, and the like. Based on the treatment planning image, a suitable radiation therapy treatment plan is generated that includes beam geometries for implementing a planned dose distribution for one or more ROIs of the patient anatomy.

In step 502, RT system 100 begins implementation of a treatment fraction of the planned treatment, for example during a specific clinical visit. As noted above, a planned radiation therapy treatment generally includes multiple treatment fractions. In step 503, RT system 100 performs day-of-treatment imaging of the patient anatomy. Thus, in step 503, RT system 100 acquires a "day-of-treatment" 3D image of the treatment plan ROIs, such as target volume 310 and neighboring OARs and/or critical structures. The day-of-treatment 3D image includes the current geometry of patient anatomy, which can vary significantly from the original geometry of the ROIs on which the treatment plan is based.

In step 504, RT system 100 generates an adapted treatment plan for the current fraction based on the day-of-treatment 3D image. For example, in some embodiments, the current geometry of the ROIs of the patient anatomy is determined via autosegmentation of the day-of-treatment 3D image. Then, via a conventional deformable registration and a conventional automated planning process, an adapted treatment plan is generated that applies the planned dose distribution to the current geometry of the ROIs.

In step 505, RT system 100 implements the adapted treatment plan for the current treatment fraction. In some embodiments, the adapted treatment plan is performed over a single rotational arc of a gantry of RT system 100. Alternatively, in some embodiments, the adapted treatment plan is performed over multiple rotational arcs of a gantry of RT system 100. Alternatively, in some embodiments, the adapted treatment plan is performed over a fraction of a rotational arc of a gantry of RT system 100 or over multiple separate fractions of a rotational arc of the gantry. Alternatively, in some embodiments, the adapted treatment plan is performed in a static-gantry radiation therapy process, such as an IMRT or a 3D conformal radiation therapy process.

In step 506, RT system 100 determines probabilistic dose distribution for one or more ROIs for the current treatment fraction. Thus, uncertainty information associated with each dose distribution for the current treatment fraction is generated for presentation to a clinician or other user of RT system 100. In some embodiments, the uncertainty information is determined based on geometric errors associated with the deformable image registration (DIR) employed to generate the adapted treatment plan in step 505. One such embodiment is described below in conjunction with FIG. 6.

Figure 6:
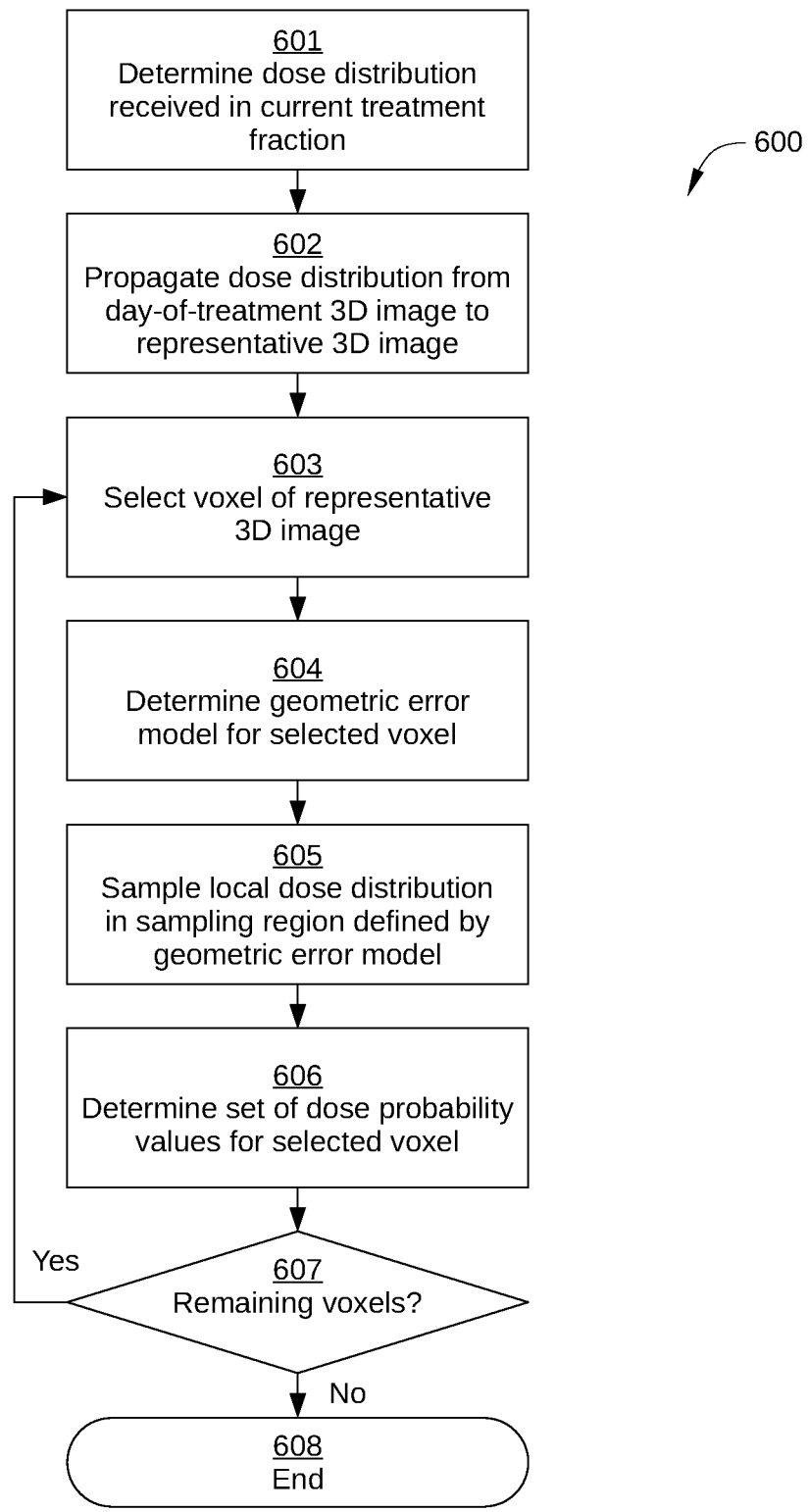
FIG. 6 sets forth a flowchart of a computer-implemented process for generating dose and associated uncertainty information for a region of patient anatomy, according to various embodiments of the present disclosure.

FIG. 6 sets forth a flowchart of a computer-implemented process 600 for generating dose and associated uncertainty information for a region of patient anatomy, according to various embodiments of the present disclosure. Computer-implemented process 600 may include one or more operations, functions, or actions as illustrated by one or more of blocks 601-608. Although the blocks are illustrated in a sequential order, these blocks may be performed in parallel, and/or in a different order than those described herein. Also, the various blocks may be combined into fewer blocks, divided into additional blocks, and/or eliminated based upon the desired implementation. Although computer-implemented process 600 is described in conjunction with RT system 100 and FIGS. 1-5, persons skilled in the art will understand that any suitably configured radiation therapy system and/or computing device is within the scope of the present embodiments.

In step 601, RT system 100 determines, for each ROI of the patient anatomy, the dose distribution received in the current treatment fraction. Generally, RT system 100 determines the dose distribution for each ROI based on the day-of-treatment 3D image of the patient anatomy. For example, in some embodiments, RT system 100 determines an estimated dose for each voxel of the day-of-treatment 3D image that corresponds to a region of patient anatomy that is estimated to receive dose during the current treatment fraction. Thus, in such embodiments, a set of dose values is determined, where each value in the set of dose values indicates a dose delivered to a region of patient anatomy that corresponds to a different respective voxel of the day-of-treatment 3D image. In step 601, the estimated dose for each voxel can be determined using conventional techniques.

In step 602, RT system 100 propagates the dose distributions for each ROI from the day-of-treatment 3D image to a representative 3D image of the patient anatomy. Thus, in such embodiments, a DIR error model determines a set of dose values, where each value in the set of dose values indicates a dose delivered to a region of patient anatomy that corresponds to a different respective voxel of the representative 3D image. The representative 3D image can be any 3D image of the patient anatomy that is suitable for calculating dose distribution of ROIs. In some embodiments, the treatment planning image is employed as the representative 3D image. Alternatively, in other embodiments, a more recently acquired 3D image of the patient anatomy is employed as the representative 3D image, for example via conventional forward propagation techniques.

In some embodiments, DIR is employed to propagate the dose distributions for each ROI from the day-of-treatment 3D image to a representative 3D image of the patient anatomy. Generally, there is no one-to-one correspondence between the voxels of the day-of-treatment 3D image and the representative 3D image of the patient anatomy, even though the region of patient anatomy in each 3D image is substantially the same. Instead, the DIR process generally includes algorithmic estimates of which voxels in one 3D image correspond to which voxels in the other 3D image. Thus, a region of patient anatomy that corresponds to a single voxel in the day-of-treatment 3D image can be represented by multiple voxels in the representative 3D image and vice-versa. Further, the position of a particular region of patient anatomy or voxel in the day-of-treatment 3D image may be incorrectly placed in the representative 3D image. As a result, the DIR process introduces significant geometric error between 3D images, and, in regions of significant dose gradient, such geometric error directly affects the accuracy of propagated dose distribution reported with respect to the representative 3D image. Further, such geometric errors are exacerbated for voxels that are not associated with anatomical or other features that are algorithmically interpretable, such as boundaries of organs or other structures, fiducials, distinct and relatively small features of organs, or other structures that can be precisely mapped from one 3D image to another. Such geometric error is described in greater detail below in conjunction with FIG. 7.

Figure 7:
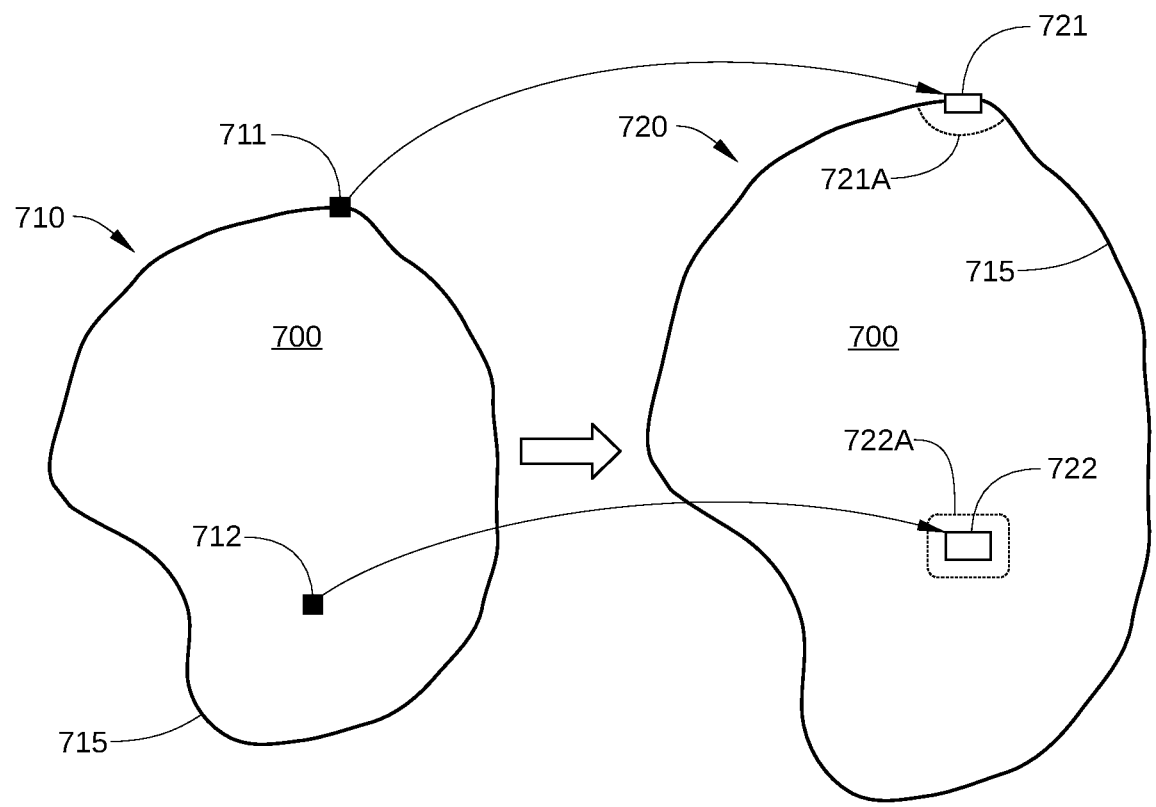
FIG. 7 schematically illustrates the transformation of anatomical locations associated with a first image of a region of interest to corresponding locations associated with a second image of the region of interest.

FIG. 7 schematically illustrates the transformation of anatomical locations associated with a first image 710 of an ROI 700 to corresponding locations associated with a second image 720 of ROI 700. For example, in one instance, first image 710 of ROI 700 may be a day-of-treatment 3D image of ROI 700, while second image 710 is a representative 3D image of ROI 700. For clarity, in FIG. 7 first image 710 and second image 720 are each depicted as two-dimensional structures. However, in practice, first image 710 and second image 720 are 3D images that each include a 3D array of voxels.

As shown, a first point 711 in first image 710 is transformed via a deformable registration process to a corresponding first region 721 in second image 720, and a second point 712 in first image 710 is transformed via the deformable registration process to a corresponding second region 722 in second image 720. In the instance illustrated in FIG. 7, first region 721 corresponds to a set of multiple voxels and second region 722 corresponds to a set of multiple voxels, while in other instances, first region 721 and second region 722 may each correspond to a single voxel in second image 720. Because first point 711 is associated with an interpretable feature, such as a boundary 715 of ROI 700, geometric error 721A (indicated schematically by dashed lines) for first region 721 can be quantified using conventional techniques or algorithms. By contrast, second point 712 is disposed within ROI 700, and is not associated with an interpretable feature of ROI 700. Consequently, geometric error 722A for second region 722 generally cannot be accurately quantified using conventional techniques or algorithms.

Returning to FIG. 6, in step 603, RT system 100 selects a particular voxel of the representative 3D image of the patient anatomy. In step 604, RT system 100 determines a geometric error model for the voxel selected in step 603. For the selected voxel, the geometric error model indicates geometric error between the selected voxel of the representative 3D image of the patient anatomy and one or more voxels of the day-of-treatment 3D image of the patient anatomy for the current treatment fraction. In some embodiments, the geometric error model for a particular voxel of the representative 3D image indicates either a measured geometric error or an assumed geometric error for that particular voxel. In such embodiments, the geometric error model indicates a measured geometric error for the particular voxel when the particular voxel is included in an interpretable feature within the representative 3D image, and such a measured geometric error can be determined based on DIR error using conventional techniques or algorithms. Alternatively, in some embodiments, the geometric error model indicates an assumed geometric error for the particular voxel when the particular voxel is not included in an interpretable feature within the representative 3D image. In such embodiments, the assumed geometric error is represented by a region of the representative 3D image that includes a plurality of voxels proximate the particular voxel. In such embodiments, a size of the region is a function of a distance of the particular voxel from an interpretable feature included in the representative 3D image. Thus, in such embodiments, the effect on dose distribution of the geometric error for a particular voxel of the representative 3D image is based on a distance of that particular voxel from one or more interpretable features of the patient anatomy, such as an ROI boundary. One such geometric error model is described below in conjunction with FIGS. 8 and 9.

Figure 8:
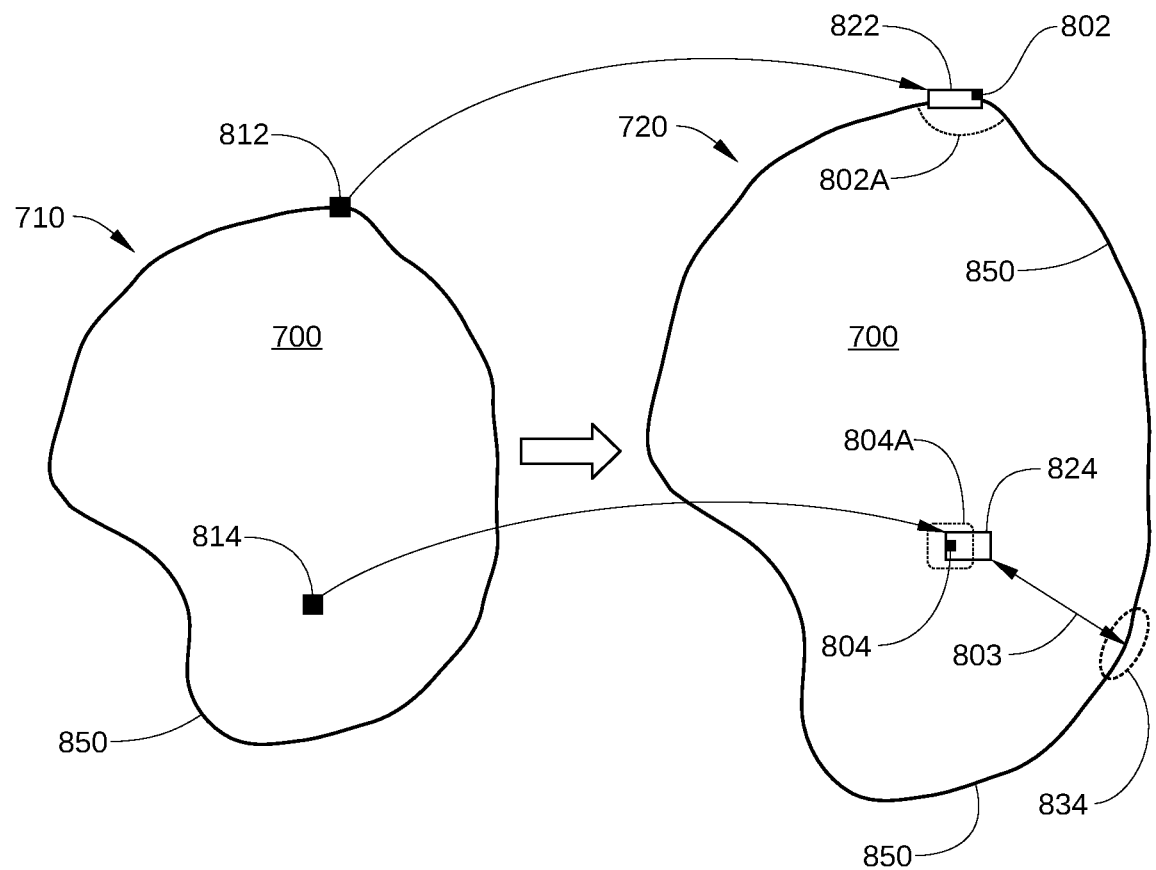
FIG. 8 schematically illustrates elements of a deformable image registration error model used for transformation of anatomical locations associated with the first image of FIG. 7 to corresponding locations associated with the second image of FIG. 7, according to various embodiments of the present disclosure.

FIG. 8 schematically illustrates elements of a geometric error model used for transformation of anatomical locations associated with first image 710 to corresponding locations associated with second image 720 of ROI 700, according to various embodiments of the present disclosure. As noted above, for certain voxels of second image 720, the geometric error model indicates a measured geometric error, and for other voxels of second image 720 the geometric error model indicates an assumed geometric error for that particular voxel.

In some embodiments, geometric error for a particular voxel of second image 720 is based on measured geometric error. For example, in some instances, a voxel 802 of second image 720 corresponds to a portion 822 of second image 720 that is an interpretable feature, such as an ROI boundary 850. In addition, portion 822 of second image 720 is mapped to a portion 812 of first image 710 by a conventional structure-guided DIR process, where portion 812 can be a single voxel or a group of multiple voxels associated with ROI boundary 850. In such an instance, a registration error (i.e., a measured geometric error 802A) between voxel 802 and portion 812 can be computed using conventional techniques.

In some embodiments, geometric error for a particular voxel of second image 720 is based on an assumed geometric error. For example, in some instances, a voxel 804 of second image 720 corresponds to a portion 824 of second image 720 that is disposed a distance 803 from an interpretable feature, such as ROI boundary 850. In addition, portion 824 of second image 720 is mapped to or associated with a portion 814 of first image 710 by a conventional structure-guided DIR process, where portion 814 does not correspond to an interpretable feature of ROI 700. Portion 814 can be a single voxel or a group of multiple voxels of first image 710 that are associated with a portion of ROI 700 that is not an interpretable feature of ROI 700, such as a center portion of RIO 700. In such an instance, an assumed geometric error between voxel 804 and portion 814 is represented by a sampling region 804A of second image 720 that includes a plurality of voxels proximate voxel 804. In such embodiments, a size of sampling region 804A is a function of a distance of voxel 804 from an interpretable feature included in the representative 3D image. For example, in the embodiment illustrated in FIG. 8, the size of sampling region 804A is determined as a function of distance 803 from ROI boundary 850. Specifically, in such embodiments, an assumed geometric error for voxel 804 increases when distance 803 increases. Examples of such embodiments are described below in conjunction with FIG. 9.

Figure 9:
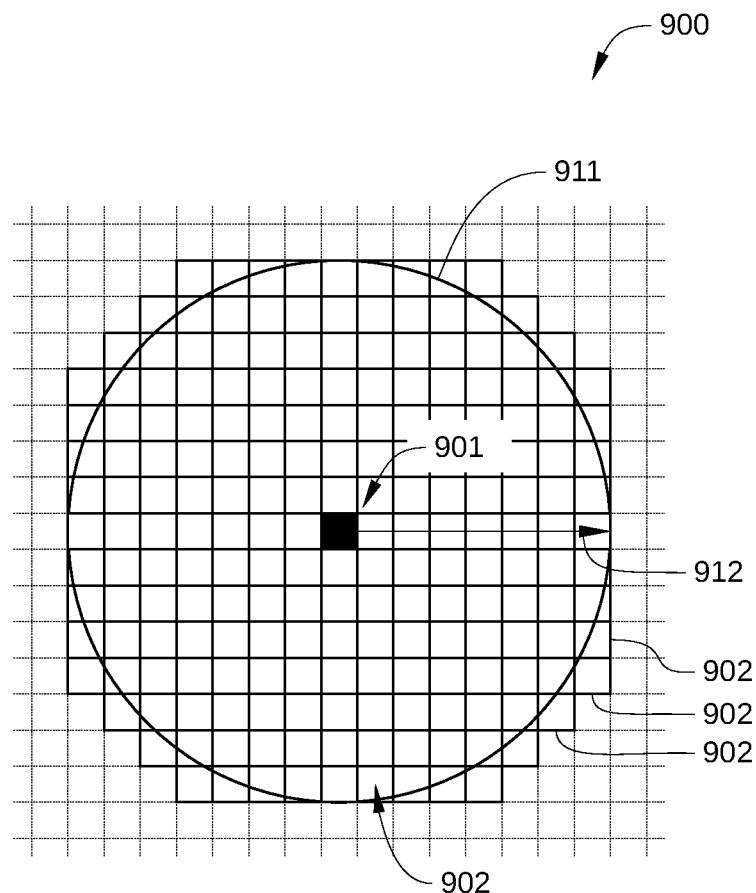
FIG. 9 schematically illustrates a probability kernel for determining an assumed geometric error for a voxel of a representative 3D image, according to various embodiments of the present disclosure.

FIG. 9 schematically illustrates a sampling region 900 that represents an assumed geometric error for a voxel 901 of a representative 3D image (not shown), according to various embodiments of the present disclosure. In the embodiment illustrated in FIG. 9, sampling region 900 is depicted as a circular area 911 that has a radius 912 and includes a plurality of voxels 902 of the representative 3D image that are proximate voxel 901. In practice, sampling region 900 is generally implemented as a 3D region, such as a sphere, ellipsoid, or other 3D shape, but for clarity sampling region 900 is depicted as a two-dimensional area in FIG. 9.

As noted above, sampling region 900 is associated with a particular voxel of the representative image, such as voxel 901. Further, the size of sampling region 900 is a function of a distance of voxel 901 from an interpretable feature (not shown) within the representative 3D image that includes voxel 901. For example, in some embodiments, the magnitude of radius 912 is a function of a distance of voxel 901 is the interpretable feature. Thus, in such embodiments, as the distance of voxel 901 from the nearest interpretable feature increases, the magnitude of radius 912 increases, and more voxels 902 are included in sampling region 900. In another example, in some embodiments, sampling region 900 is implemented as an ellipsoid or other shape that is not symmetrical in three dimensions. In such embodiments, as the distance of voxel 901 from the nearest interpretable feature increases, the magnitude of multiple axes or dimensions of sampling region 900 increases. In such embodiments, the increase in such axes or dimensions may not be uniform based on one or more factors that can affect geometric error, such as distance to a secondary interpretable feature, etc.

Returning to FIG. 6, in step 605, RT system 100 samples a local dose distribution in a sampling region determined for the particular voxel of the representative 3D image selected in step 603, such as voxel 901 of FIG. 9. Specifically, the dose value determined in step 602 for each voxel included in the sampling region is sampled or otherwise retrieved. For example, when voxel 901 is the selected voxel, the propagated dose value for voxels 902 that included in sampling region 900 are sampled or retrieved.

In step 606, RT system 100 determines a set of dose probability values for the selected voxel of the representative 3D image. For example, in some embodiments, RT system 100 determines dose probability values for the selected voxel based on the dose values sampled in step 605. In some embodiments, the set of dose probability values includes a plurality of dose bins and, for each dose bin, a corresponding probability value. Together, the set of dose probability values provide a probabilistic dose distribution for the selected voxel. One embodiment of a probabilistic dose distribution is described below in conjunction with FIG. 10.

Figure 10:
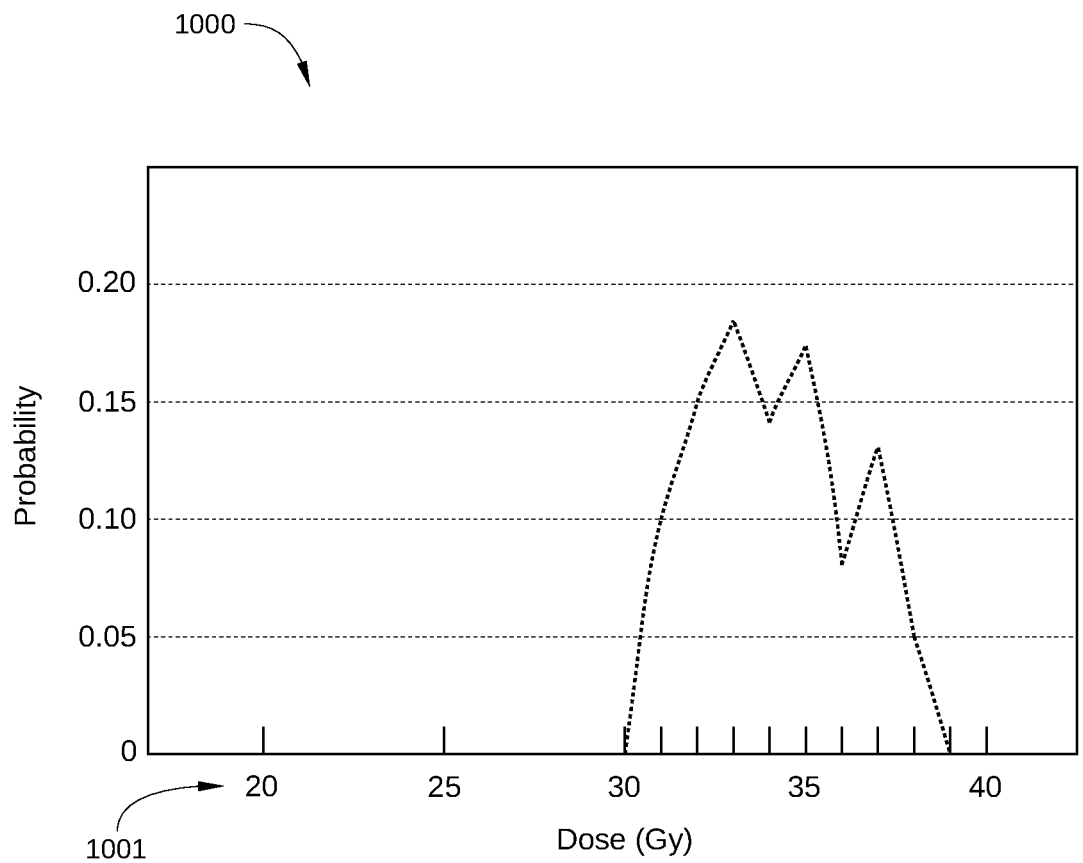
FIG. 10 schematically illustrates a probabilistic dose distribution for a voxel of a representative 3D image of patient anatomy, according to various embodiments of the present disclosure.

FIG. 10 schematically illustrates a probabilistic dose distribution 1000 for a voxel of a representative 3D image of patient anatomy, according to various embodiments of the present disclosure. Probabilistic dose distribution 1000 graphically represents the set of dose probability values determined in step 605 for a particular voxel of a representative 3D image. In the embodiment illustrated in FIG. 10, probabilistic dose distribution 1000 includes a value for each of a plurality of dose bins 1001 from 0 to 100 Gy that are plotted along a horizontal axis. Thus, in probabilistic dose distribution 1000, column height for each particular dose bin 1001 (for example, 0 Gy, 1 Gy, 2 Gy, etc.) indicates a probability that the voxel associated with probabilistic dose distribution 1000 has received a dose corresponding to that particular dose bin 1001. For example, in the embodiment illustrated in FIG. 10, based on the dose values sampled in step 605 for the currently selected voxel, there is a 10% probability that the currently selected voxel received a dose of 31 Gy, a 15% probability that the currently selected voxel received a dose of 32 Gy, an 18% probability that the currently selected voxel received a dose of 33 Gy, and so on. It is noted that when a selected voxel is disposed in a high dose-gradient region, probabilistic dose distribution 1000 can include a much wider range of dose bins 1001 than depicted in FIG. 10.

In some embodiments, probabilistic dose distribution 1000 is generated for a particular voxel via a probability model, such as a kernel or other weighting function. In such embodiments, each entry of the kernel or weighting function can correspond to a different voxel that is sampled in step 605. In such embodiments, when a uniform probability distribution is assumed within the sampling region of the selected voxel, the propagated dose value of each sampled voxel has equal weight when determining the dose probability values of probabilistic dose distribution 1000. Alternatively, in such embodiments, when a non-uniform probability distribution is assumed within the sampling region of the selected voxel, the propagated dose value of each sampled voxel can have a different weight when determining the dose probability values of probabilistic dose distribution 1000. For example, a normal or Gaussian distribution may be assumed for the propagated dose value of each sampled voxel, so that the propagated dose values of sampled voxels that are closer to the selected voxel have more effect on the dose probability values of probabilistic dose distribution 1000 than the propagated dose values of sampled voxels that are farther from the selected voxel.

In step 607, RT system 100 determines whether there are any remaining voxels in the representative 3D image for which dose and associated uncertainty information have not been determined. If yes, method 600 returns to step 603; if no, method 600 proceeds to step 608 and terminates.

Implementation of computer-implemented process 600 enables the generation of delivered dose and associated uncertainty information for one or more ROI's of patient anatomy. As a result, the delivered dose information and dose uncertainty information can be presented together in the dose domain to a clinician or other user of RT system 100, thereby facilitating clinician interpretation of the dose information.

Returning to FIG. 5, in step 507, RT system 100 reports probabilistic dose distribution information for the current treatment fraction. In some embodiments, RT system 100 can report the probabilistic dose distribution information for one or more ROIs. Such probabilistic dose distribution information includes dose information for the ROI and dose probability information for the ROI. For example, in some embodiments, the probabilistic dose distribution information is presented as a dose-volume histogram. One such embodiment is illustrated in FIG. 11.

Figure 11:
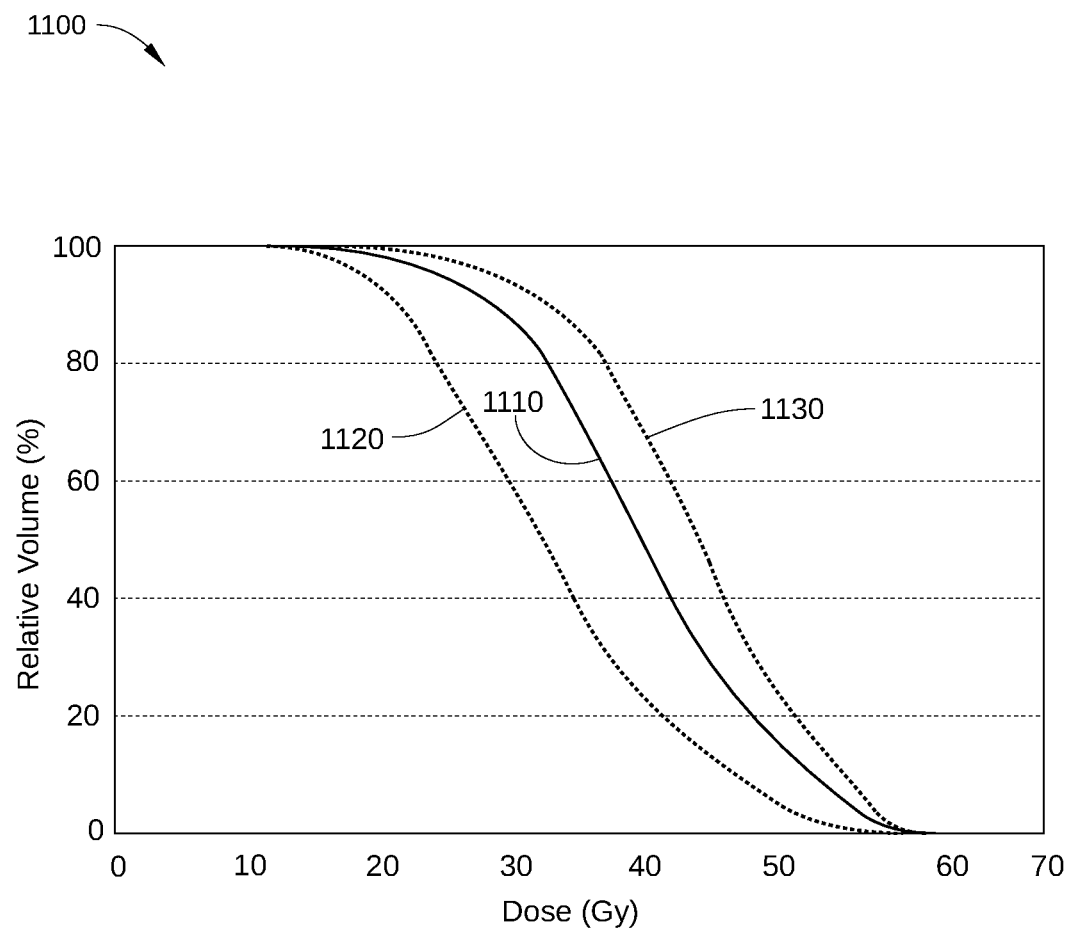
FIG. 11 illustrates a dose-volume histogram, according to various embodiments of the present disclosure.

FIG. 11 illustrates a dose-volume histogram (DVH) 1100, according to various embodiments of the present disclosure. DVH 1100 relates, in a two-dimensional format, the delivered dose for a specific treatment fraction to a particular ROI (such as a PTV, GTV, OAR, or other structure). In addition, DVH 1100 indicates dose uncertainty information associated with the delivered dose for that particular ROI. Consequently, DVH 1100 enables a clear understanding of the uncertainty of delivered dose for the ROI, such as the most likely delivered dose, the worst-case delivered dose (such as a maximum delivered dose to an OAR or a minimum delivered dose to a PTV), the best-case delivered dose (such as a minimum delivered dose to an OAR or a maximum delivered dose to a PTV), and the like.

A DVH includes dose information for a plurality of dose bins and can be implemented as either a differential DVH or a cumulative DVH. In the embodiment illustrated in FIG. 11, DVH 1100 is a cumulative DVH, and includes a value for each of a plurality of dose bins from 20 to 40 Gy that are plotted along a horizontal axis. In DVH 1100, column height for each bin (for example, 0 Gy, 1 Gy, 2 Gy, etc.) indicates a volume of a particular structure receiving greater than or equal to that dose value. For example, the column height of the second bin (1 Gy) represents the volume of the particular structure receiving greater than or equal to that dose. Thus, with a large number of small bin sizes, each dose-volume objective included in DVH 1100 substantially appears to be a smooth curve.

In the embodiment illustrated in FIG. 11, DVH 1100 includes multiple dose distributions for a specific OAR and a specific treatment fraction. Specifically, DVH includes a most-likely dose distribution 1110, a best-case dose distribution 1120, and a worst-case dose distribution 1130. In the embodiment, most-likely dose distribution 1110 represents a mean of the probabilistic dose distribution for the specific OAR, best-case dose distribution 1120 represents a fifth percentile of the probabilistic dose distribution for the specific OAR, and worst-case dose distribution 1130 represents a ninety-fifth percentile of the probabilistic dose distribution for the specific OAR. Thus, for each dose bin, DVH 1100 includes multiple dose values. In the embodiment illustrated in FIG. 11, the multiple dose values are a dose value that corresponds to a mean of the probabilistic dose distribution, a dose value that corresponds to a fifth percentile of the probabilistic dose distribution, and a dose value that corresponds to a ninety-fifth percentile of the probabilistic dose distribution. More generally, in some embodiments, the multiple dose values for a particular dose bin can include a mean dose value of the probabilistic dose distribution $\overline{D}(x)$, where $\overline{D}(x)=E[D(x)]$, a highest likely dose value of the probabilistic dose distribution that equals $D(x)+cs(x)$, and a lowest likely dose value of the probabilistic dose distribution that equals $D(x)-cs(x)$, where $s(x)=\sqrt{Var[D(x)]}$.

In some embodiments, DVH 1100 may further include one or more dose-volume objectives (not shown), such as a maximum allowable dose indicator or a target minimum dose threshold indicator. Thus, in such embodiments, a clinician can readily compare the various clinical goals for an ROI (e.g., most-likely dose distribution 1110, best-case dose distribution 1120, and worst-case dose distribution 1130) to the different possible dose distributions for the ROI.

In some embodiments, an individual curve representing a dose distribution for a specified probability (e.g., best-case dose distribution 1120 or worst-case dose distribution 1130) is generated based on the sets of dose probability values for the voxels of the representative 3D image. Specifically, dose from each voxel of the representative 3D image is read for the specified probability, then the voxels that include a dose at the specified probability are included in the dose distribution. In this way, a 5-percentile dose distribution curve, a 95-percentile dose distribution curve, and the like can be constructed based on the set of dose probability values for the voxels of the representative 3D image. Alternatively or additionally, in some embodiments, any other technically feasible approach can be employed for displaying information included in the sets of dose probability values for the voxels of the representative 3D image. For example, dose information can be displayed for a specified probability in a 3D image of an ROI or other portion of patient anatomy within the representative 3D image. In such embodiments, portions of the ROI are shown that have at least a specified probability of having received the displayed dose, such as a 5-percentile dose map, a 10-percentile dose, map, etc. Further, in such embodiments, multiple such 3D images for different probabilities can be generated, so that a clinician or other user can navigate through such images with a slider or other selection mechanism.

Returning to FIG. 5, in optional step 508, RT system 100 determines and reports accumulated probabilistic dose distribution information for some or all of the currently completed treatment fractions. In such embodiments, the accumulated probabilistic dose distribution information can be presented similarly to the probabilistic dose distribution information for that is reported for the treatment fraction in step 507. Thus, a clinician can directly monitor accumulated dose for one or more ROIs as a planned treatment progresses through multiple fractions. In some embodiments, clinical analysis based on such monitoring can inform continuation of the current planned treatment, such as when an OAR receives too much dose and a modified treatment plan is indicated.

In step 510, the determination is made whether there are any remaining treatment fractions to be performed. For example, a clinician may make such a determination based on information obtained in step 508 and/or whether all planned treatment fractions have been performed. If yes, ART process 500 returns to step 502; if no, ART process 500 proceeds to step 520.

In step 520, RT system 100 determines and reports accumulated probabilistic dose distribution information for some or all of the currently completed treatment fractions. In such embodiments, the accumulated probabilistic dose distribution information can be presented similarly to the probabilistic dose distribution information for that is reported for the treatment fraction in step 507.

Example Computing Device

Figure 12:
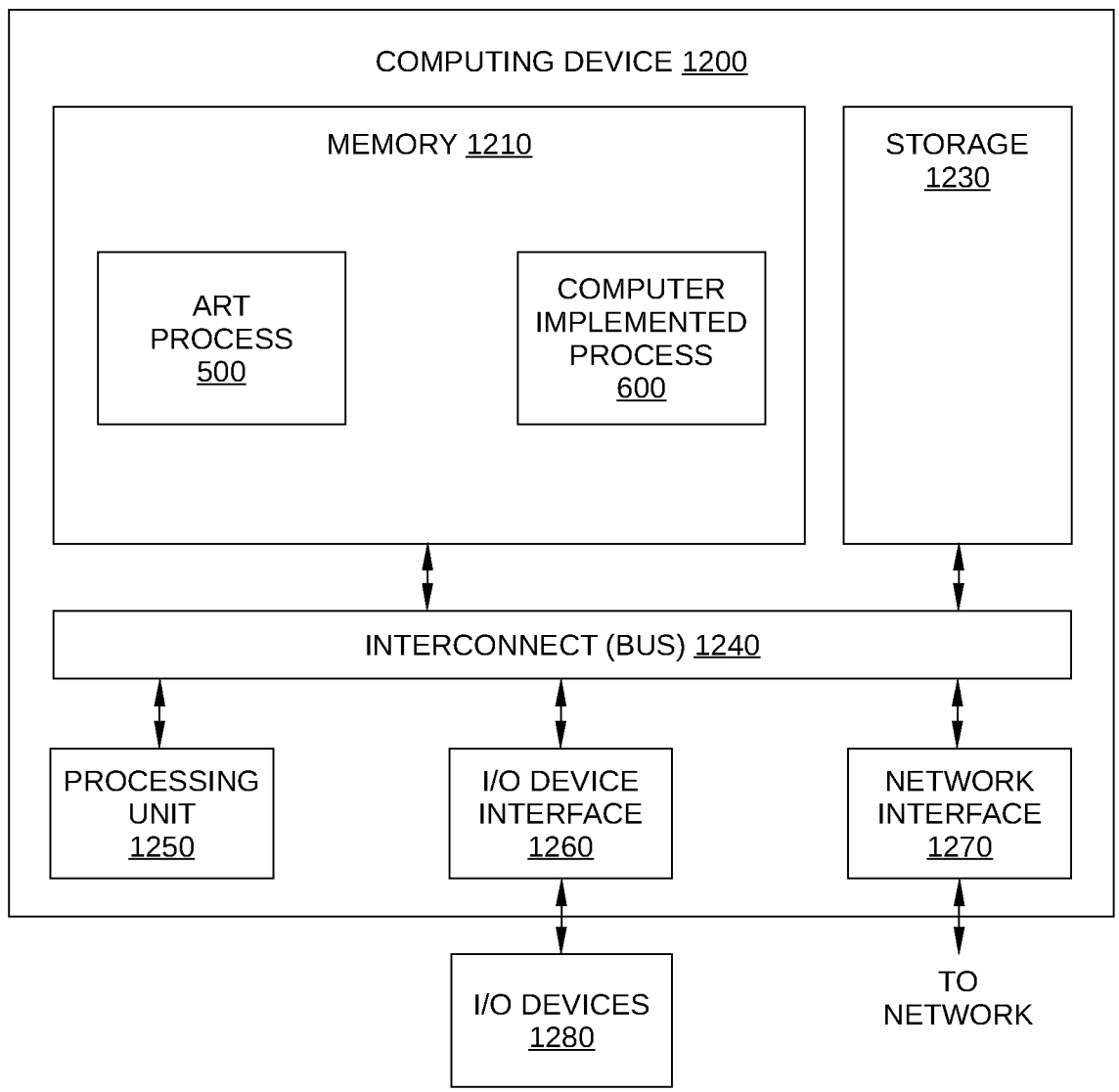
FIG. 12 is an illustration of a computing device configured to perform various embodiments of the present disclosure.

FIG. 12 is an illustration of computing device 1200 configured to perform various embodiments of the present disclosure. For example, in some embodiments, computing device 1200 can be implemented as image acquisition and treatment control computer 106 and/or remote control console 110 in FIG. 1. Computing device 1200 may be a desktop computer, a laptop computer, a smart phone, or any other type of computing device suitable for practicing one or more embodiments of the present disclosure. In operation, computing device 1200 is configured to execute instructions associated with ART process 500 and/or computer-implemented process 600 as described herein. It is noted that the computing device described herein is illustrative and that any other technically feasible configurations fall within the scope of the present disclosure.

As shown, computing device 1200 includes, without limitation, an interconnect (bus) 1240 that connects a processing unit 1250, an input/output (I/O) device interface 1260 coupled to input/output (I/O) devices 1280, memory 1210, a storage 1230, and a network interface 1270. Processing unit 1250 may be any suitable processor implemented as a central processing unit (CPU), a graphics processing unit (GPU), an application-specific integrated circuit (ASIC), a field programmable gate array (FPGA), any other type of processing unit, or a combination of different processing units, such as a CPU configured to operate in conjunction with a GPU or digital signal processor (DSP). In general, processing unit 1250 may be any technically feasible hardware unit capable of processing data and/or executing software applications, including ART process 500 and/or computer-implemented process 600.

I/O devices 1280 may include devices capable of providing input, such as a keyboard, a mouse, a touch-sensitive screen, and so forth, as well as devices capable of providing output, such as a display device and the like. Additionally, I/O devices 1280 may include devices capable of both receiving input and providing output, such as a touchscreen, a universal serial bus (USB) port, and so forth. I/O devices 1280 may be configured to receive various types of input from an end-user of computing device 1200, and to also provide various types of output to the end-user of computing device 1200, such as displayed digital images or digital videos. In some embodiments, one or more of I/O devices 1280 are configured to couple computing device 1200 to a network.

Memory 1210 may include a random access memory (RAM) module, a flash memory unit, or any other type of memory unit or combination thereof. Processing unit 1250, I/O device interface 1260, and network interface 1270 are configured to read data from and write data to memory 1210. Memory 1210 includes various software programs that can be executed by processor 1250 and application data associated with said software programs, including ART process 500 and/or computer-implemented process 600.

Example Computer Program Product

Figure 13:
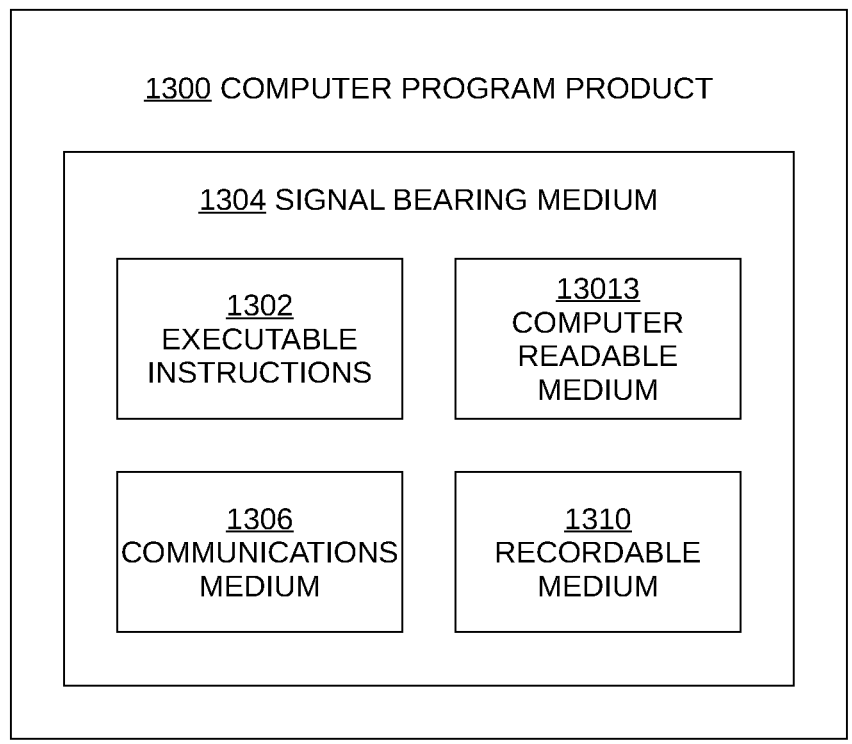
FIG. 13 is a block diagram of an illustrative embodiment of a computer program product for implementing methods according to various embodiments of the present disclosure.

FIG. 13 is a block diagram of an illustrative embodiment of a computer program product 1300 for implementing methods according to various embodiments of the present disclosure. Computer program product 1300 may include a signal bearing medium 1304. Signal bearing medium 1304 may include one or more sets of executable instructions 1302 that, when executed by, for example, a processor of a computing device, may provide at least the functionality described above with respect to FIGS. 1-12.

In some implementations, signal bearing medium 1304 may encompass a non-transitory computer readable medium 1308, such as, but not limited to, a hard disk drive, a Compact Disc (CD), a Digital Video Disk (DVD), a digital tape, memory, etc. In some implementations, signal bearing medium 1304 may encompass a recordable medium 1310, such as, but not limited to, memory, solid-state drives, read/write (R/W) CDs, R/W DVDs, etc. In some implementations, signal bearing medium 1304 may encompass a communications medium 1306, such as, but not limited to, a digital and/or an analog communication medium (e.g., a fiber optic cable, a waveguide, a wired communications link, a wireless communication link, etc.). Computer program product 1300 may be recorded on non-transitory computer readable medium 1308 or another similar recordable medium 1310.

In sum, embodiments described herein determine uncertainty in the dose distribution that is delivered to one or more ROIs during a particular adaptive radiotherapy treatment fraction. Further, the uncertainty in the accumulated dose associated with multiple adaptive radiotherapy treatment fractions can also be determined. As a result, the embodiments facilitate more accurate planning for re-treatments and enable better clinician understanding of the relationship between an outcome and the actual delivered dose. These technical advantages provide one or more technological advancements over prior art approaches.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, a solid-state drive, or any suitable combination of the foregoing. In the context of this document, a computer readable storage medium may be any tangible medium that can contain, or store a program for use by or in connection with an instruction execution system, apparatus, or device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

We claim:

1. A computer-implemented method of generating dose information for a region of patient anatomy, the method comprising:
   determining a first set of dose values for a day-of-treatment three-dimensional (3D) image of the region, wherein each value in the first set of dose values is associated with a different voxel of the first 3D image, and wherein the day-of-treatment 3D image is associated with a specific application of dose to the region for a treatment fraction;
   determining a second set of dose values for a representative 3D image of the region, wherein the representative 3D image corresponds to a treatment planning image of the region obtained prior to the day-of-treatment 3D image, and each value in the second set of dose values is associated with a different voxel of the representative 3D image;
   determining a set of geometric error models for the representative 3D image of the region, wherein each geometric error model in the set of geometric error models indicates a geometric error between a voxel of the representative 3D image and one or more voxels of the day-of-treatment 3D image of the region for the treatment fraction;
   based on the second set of dose values and the set of geometric error models, determining a set of dose probability values for each voxel of the representative 3D image, wherein each set of dose probability values includes at least one dose value and a probability value that a voxel of the representative 3D image corresponds to the dose value; and
   presenting a delivered dose distribution for a portion of the representative 3D image and uncertainty information associated with the delivered dose distribution to a clinician, wherein the uncertainty information is based on the sets of dose probability values.

2. The computer-implemented method of claim 1, wherein determining the set of dose probability values for each voxel of the representative 3D image comprises:
   determining a sampling region of the representative 3D image that is proximate the voxel of the representative 3D image; and
   sampling a dose value from the second set of dose values for each voxel within the sampling region.

3. The computer-implemented method of claim 1, wherein each set of dose probability values comprises a probabilistic dose distribution.

4. The computer-implemented method of claim 1, wherein each geometric error model in the set of geometric error models indicates one of a measured geometric error between a particular voxel of the representative 3D image and one or more voxels of the day-of-treatment 3D image of the region for the treatment fraction or an assumed geometric error between the particular voxel and one or more voxels of the day-of-treatment 3D image of the region for the treatment fraction.

5. The computer-implemented method of claim 1, further comprising generating a dose-volume histogram for the region that is based on the sets of dose probability values determined for the voxels of the representative 3D image.

6. The computer-implemented method of claim 1, wherein the portion of the representative 3D image comprises a region of interest included in the representative 3D image.

7. The computer-implemented method of claim 1, wherein the delivered dose distribution for the portion of the representative 3D image comprises dose delivered over a specific single treatment fraction.

8. The computer-implemented method of claim 1, wherein the delivered dose distribution for the portion of the representative 3D image comprises dose accumulated over multiple treatment fractions.

9. The computer-implemented method of claim 1, wherein determining the second set of dose values for the representative 3D image comprises propagating the first set of dose values to the voxels of the representative 3D image.

10. The method of claim 1, wherein the uncertainty information is associated with geometric error between one or more voxels of the representative 3D image and one or more voxels of the day-of-treatment 3D image of the region for the treatment fraction.

11. The computer-implemented method of claim 2, wherein determining the sampling region comprises determining the sampling region based on a geometric error model for the voxel of the representative 3D image.

12. The computer-implemented method of claim 2, wherein determining the set of dose probability values for each voxel of the representative 3D image further comprises determining a probability value for each dose bin in the set of dose probability values based on the dose values sampled from the second set of dose values.

13. The computer-implemented method of claim 4, wherein a geometric error model in the set of geometric error models indicates a specific measured geometric error between the particular voxel of the representative 3D image and one or more voxels of the day-of-treatment 3D image of the region for the treatment fraction when the particular voxel is included in an interpretable feature within the representative 3D image.

14. The computer-implemented method of claim 4, wherein a geometric error model in the set of geometric error models indicates a specific assumed geometric error between the particular voxel of the representative 3D image and one or more voxels of the day-of-treatment 3D image of the region for the treatment fraction when the particular voxel is not included in an interpretable feature within the representative 3D image.

15. The computer-implemented method of claim 4, wherein the assumed geometric error is represented by a region of the representative 3D image that includes a plurality of voxels proximate the particular voxel.

16. The computer-implemented method of claim 5, wherein the dose-volume histogram includes, for each dose bin of the dose-volume histogram, probability information for the dose bin.

17. The computer-implemented method of claim 12, wherein determining the probability value for each dose bin in the set of dose probability values comprises applying a weighting function to the dose values sampled from the second set of dose values.

18. The computer-implemented method of claim 15, wherein a size of the region is a function of a distance of the particular voxel from an interpretable feature included in the representative 3D image.

19. The computer-implemented method of claim 16, wherein the probability information for the dose bin includes one or more of a mean dose value that corresponds to a mean of the probabilistic dose distribution for the dose bin, a highest likely dose value that corresponds to a high percentile of the probabilistic dose distribution for the dose bin, or a lowest likely dose value that corresponds to a high percentile of the probabilistic dose distribution for the dose bin.

20. A non-transitory computer-readable medium having instructions stored thereon, which in response to execution by one or more processors, cause the one or more processors to perform or control performance of a method of generating dose information for a region of patient anatomy, wherein the method comprises:

determining a first set of dose values for a day-of-treatment three-dimensional (3D) image of the region, wherein each value in the first set of dose values is associated with a different voxel of the first 3D image, and wherein the day-of-treatment 3D image is associated with a specific application of dose to the region for a treatment fraction;

determining a second set of dose values for a representative 3D image of the region, wherein the representative 3D image corresponds to a treatment planning image of the region obtained prior to the day-of-treatment 3D image, and each value in the second set of dose values is associated with a different voxel of the representative 3D image;

determining a set of geometric error models for the representative 3D image of the region, wherein each geometric error model in the set of geometric error models indicates a geometric error between a voxel of the representative 3D image and one or more voxels of the day-of-treatment 3D image of the region;

based on the second set of dose values and the set of geometric error models, determining a set of dose probability values for each voxel of the representative 3D image, wherein each set of dose probability values includes at least one dose value and a probability value that a voxel of the representative 3D image corresponds to the dose value; and presenting a delivered dose distribution for a portion of the representative 3D image and uncertainty information associated with the delivered dose distribution to a clinician, wherein the uncertainty information is based on the sets of dose probability values.

* * * * *